United States Patent
Ferree

(10) Patent No.: US 6,645,247 B2
(45) Date of Patent: Nov. 11, 2003

(54) SUPPLEMENTING ENGINEERED ANNULUS TISSUES WITH AUTOGRAFT OF ALLOGRAFT TENDONS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/167,503

(22) Filed: Jun. 13, 2002

(65) Prior Publication Data

US 2002/0156532 A1 Oct. 24, 2002

Related U.S. Application Data

(63) Continuation-in-part of application No. 09/688,716, filed on Oct. 16, 2000, now Pat. No. 6,454,804, and a continuation-in-part of application No. 09/638,726, filed on Aug. 14, 2000, now Pat. No. 6,340,369, and a continuation-in-part of application No. 09/415,382, filed on Oct. 8, 1999, now Pat. No. 6,419,704.

(60) Provisional application No. 60/159,488, filed on Oct. 14, 1999, and provisional application No. 60/371,546, filed on Apr. 10, 2002.

(51) Int. Cl.$^7$ .................................................. A61F 2/44
(52) U.S. Cl. .................... 623/17.11; 623/908; 404/93.7
(58) Field of Search .......................... 623/17.11–17.16, 623/919, 908, 13.11; 424/93.7

(56) References Cited

U.S. PATENT DOCUMENTS

| | | | | |
|---|---|---|---|---|
| 4,349,921 A | * | 9/1982 | Kuntz | 623/17.16 |
| 4,950,296 A | * | 8/1990 | McIntyre | 623/23.63 |
| 6,248,131 B1 | * | 6/2001 | Felt et al. | 623/17.12 |
| 6,264,695 B1 | * | 7/2001 | Stoy | 623/17.16 |
| 6,419,704 B1 | * | 7/2002 | Ferree | 623/17.12 |
| 6,454,804 B1 | * | 9/2002 | Ferree | 623/17.11 |
| 6,503,277 B2 | * | 1/2003 | Bonutti | 623/11.11 |

OTHER PUBLICATIONS

North American Spine Society 13 Annual Meeting, San Francisco Hilton and Towers. Oct. 28–31, 1998; Barron Lonner Md., Et. al., "Tissue Engineered Regeneration of the Intervertebral Disc".

Orthopedics Today, Jul. 2000.

"Proceedings 14th Annual Meeting" North American Spine Society, Oct. 1999.

"Proceedings 13th annual Meeting" North American Spine Society, Oct. 1998.

Steven Frick MD, SPINE vol. 19, No. 16, pp. 1826–1835, 1994.

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Fibrocytes, annulus fibrosis cells, cells that differentiate into annulus fibrosis cells, or cells that function like annulus fibrosis cells are harvested and combined with the extracellular matrix of the annulus fibrosis from a recently deceased human or animal to produce an engineered annulus fibrosis. Autograft tendons are then used to strengthen the annulus fibrosis and to augment or replace the nucleus pulpous. In accordance with a preferred embodiment, tendons such as the palmaris longus are harvested from the patient, a suitable living donor, or a recently deceased human. The tendons are sewn or otherwise attached to the inside of the annulus fibrosis using percutaneous or laparoscopic procedures. The tendons aid the nucleus and/or replace the nucleus by absorbing the compression forces between vertebrae and by transferring the compression forces to the augmented annulus fibrosis. Allograft tendons are preferably treated, with tissue banking techniques well known to those skilled in the art, to prevent disease transmission and graft rejection. The invention can be used to augment discs in the cervical, thoracic, or lumbar spine.

13 Claims, No Drawings

SUPPLEMENTING ENGINEERED ANNULUS TISSUES WITH AUTOGRAFT OF ALLOGRAFT TENDONS

REFERENCE TO RELATED APPLICATIONS

This application is a continuation-in-part of U.S. patent application Ser. No. 09/688,716, filed Oct. 16, 2000 now U.S. Pat. No. 6,454,804, which claims priority from U.S. Provisional Patent Application Serial No. 60/159,488, filed Oct. 14, 1999, and is a continuation-in-part of U.S. patent application Ser. No. 09/638,726, filed Aug. 14, 2000, now U.S. Pat. No. 6,340,369, and Ser. No. 09/415,382, filed Oct. 8, 1999 now U.S. Pat. No. 6,419,704. This application also claims priority from U.S. Provisional Patent Application Serial No. 60/371,546, filed Apr. 10, 2002; the entire content of each application and issued patent being incorporated herein by reference.

FIELD OF THE INVENTION

This invention relates generally to the treatment of diseased or traumatized intervertebral discs, and more particularly, to the use of engineered tissues in conjunction with such treatments.

BACKGROUND OF THE INVENTION

Intervertebral discs provide mobility and a cushion between the vertebrae. At the center of the disc is the nucleus pulposus. The nucleus pulposus is surrounded by the annulus fibrosis, which is comprised of cells (fibrocyte-like and chondrocyte-like), collagen fibers, and non-fibrillar extracellular matrix. The components of the annulus are arranged in 15–25 lamellae around the nucleus pulposus. The fibers in the lamellae alternate their direction of orientation by 30 degrees between each band.

The annulus fibrosis has three important functions. First, the annulus contains the nucleus pulposus. Second, the annulus fibrosis, with other ligaments, connects the vertebrae of the spine. Lastly, the annulus fibrosis helps to control movement between the vertebrae.

The fibers of the annulus can tear causing pain and possible extrusion of the nucleus pulposus. Extrusion of the nucleus pulposus is known as a disc herniation. Disc herniations can compress nerves or the spinal cord resulting in arm or leg pain and dysfunction. Surgery to repair disc herniations leaves a hole in the annulus fibrosis. The hole in the annulus acts as a pathway for additional material to protrude into a nerve, resulting in a recurrence of the herniation. My U.S. Pat. No. 6,245,107 and Patent Cooperation Treaty Application Serial No. PCT/US/14708 describe methods and devices to occlude annular defects.

To date, the treatment of tears or defects of the annulus fibrosis has relied for the most part on eliminating the defective disc or disc function. This may be accomplished by fusing the vertebra on either side of the disc.

In terms of replacement, prior-art techniques replace either the nucleus or the nucleus and annulus functions. This may be accomplished using natural or synthetic materials, or a combination of natural and artificial components. Although transplantation of living cells risks rejection by graft host reaction, certain of my previous disclosures, including those in U.S. patent application Ser. Nos. 09/688,716 and 09/638,726 (now U.S. Pat. No. 6,340,369) recognize that transplantation of the extracellular matrix of the annulus fibrosis is unlikely to incite graft host reaction. As such, fibrocytes are harvested, cultured, then added to annulus fibrosis extracellular matrix obtained from recently deceased humans or animals. The combined annulus fibrosis is then introduced into the injured or diseased disc.

The cells or engineered tissues may be introduced using any surgical technique, including percutaneous or laparoscopic approaches. As one delivery mechanism, a passageway may be formed through the annulus fibrosis, with the cells or engineered disc tissue being introduced into the disc through the passageway. In particular, the engineered disc tissue may be sewn or otherwise adhered to the inside or outside of the existing annulus fibrosis using a surgical procedure performed from the posterior or anterior portion of the body.

SUMMARY OF THE INVENTION

Certain of my co-pending patent applications and issued patents referenced above disclose the step of adding one or more substances to disc-related cells or annular tissue prior to transplantation. Such substances could include culture media, growth factors, differentiation factors, hydrogels, polymers, antibiotics, anti-inflammatory medications, immuno-suppressive medications, or any useful combination thereof. These previous disclosures further teach that such substances and materials may be combined with any compatible nucleus replacement procedure, including the embodiments described in co-pending U.S. Pat. No. 6,371,990 and the continuations thereof, all of which are incorporated herein by reference.

According to this invention, autograft or allograft tendons are used to strengthen the annulus fibrosis and to augment or replace the nucleus pulposus. In accordance with the method, tendons such as the palmaris longus are harvested from the patient, a suitable living donor, or a recently deceased human. The tendons are sewn or otherwise attached to the inside of the annulus fibrosis, through a hole in the annulus fibrosis, for example.

The tendons aid the nucleus and/or replace the nucleus by absorbing the compression forces between vertebrae and by transferring the compression forces to the augmented annulus fibrosis. Allograft tendons are preferably treated, with tissue banking techniques well known to those skilled in the art, to prevent disease transmission and graft rejection. The invention can be used to augment discs in the cervical, thoracic, or lumbar spine.

DETAILED DESCRIPTION OF THE INVENTION

Broadly according to the inventions disclosed in U.S. patent application Ser. Nos. 09/688,716 and 09/638,726 (now U.S. Pat. No. 6,340,369), fibrocytes are harvested, cultured, added to annulus fibrosis extracellular matrix material, then sewn or otherwise placed relative to an injured or diseased disc. The annulus fibrosis cells and extracellular matrix are preferably harvested from a live human, though recently deceased human or animal donors may alternatively be used. Depending upon the extent of the harvest, the recipient may function at least in part as a donor, or the tissues from others, including fetal or embryo sources, may be used.

The fibrocytes may be obtained from a tendon of the patient; for example, a palmaris longus tendon may be removed from one arm. The harvested fibrocytes are isolated and cultured using standard techniques. Precursor cells of the annulus fibrosis, annulus fibrosis cells, chondrocytes, or other living cells that could function like annulus fibrosis cells or that could differentiate into cells to build a functional annulus fibrosis may also be used. The cells from the culture are then implanted into the donor extracellular matrix to form a living annulus fibrosis. In the preferred embodiment, the cells are injected into small holes drilled into the donor extracellular matrix. In an alternative embodiment, living cells are not added to the harvested annulus fibrosis. The harvested annulus fibrosis is processed as described above to kill the living host annulus cells.

The engineered tissue may be added to the inside or the outside of the patient's annulus. Surgical procedures to access the inner or outer surface of the annulus fibrosis are well known to those skilled in the art. For example, the engineered annulus could be sutured, placed against, or "glued" to the patient's annulus. Platelet rich plasma combined with calcium and thrombin or "fibrin glue" could be used to glue the annular tissues together.

Additional substances may also be added to the transplanted annulus. For example, resorbable culture medium, tissue growth or differentiation factors (recombinant generated morphogenetic proteins, PDGF, TGF-β, EGF/TGF-α, IGF-I, βFGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be used.

As part of a further alternative embodiment, autograft or allograft tendons are used to strengthen the annulus fibrosis and to augment or replace the nucleus pulpous. In accordance with this method, tendons such as the palmaris longus are harvested from the patient, a suitable living donor, or a recently deceased human. The tendons are sewn or otherwise attached to the inside of the annulus fibrosis, through a hole in the annulus fibrosis, for example.

The tendons aid the nucleus and/or replace the nucleus by absorbing the compression forces between vertebrae and by transferring the compression forces to the augmented annulus fibrosis. Allograft tendons are preferably treated, with tissue banking techniques well known to those skilled in the art, to prevent disease transmission and graft rejection. The invention can be used to augment discs in the cervical, thoracic, or lumbar spine.

Although annulus fibrosis augmentation and/or transplantation are being described herein in detail, the invention is not limited to treatment of the intervertebral disc. For example, the invention could also be used to treat other tissues of the body such as the meniscus of the knee. In such cases, a meniscus would be removed from recently deceased humans. The harvested meniscus would be processed to kill the cells but preserve the extracellular matrix. Fibroctyes harvested as described above would then be added to the extracellular matrix prior to insertion of the engineered meniscus into a patient's knee. Similarly, chondrocytes could be harvested and added to the meniscus extracellular matrix as described in my pending U.S. patent application Ser. Nos. 09/639,309; 09/628,727; 09/638,726; and 09/638,242, all of which are incorporated herein by reference.

Similarly, the process could be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

I claim:

1. A method of treating an intervertebral disc, comprising the steps of:

harvesting autograft or allograft tendon material from a live or recently deceased human or other suitable donor; and transplanting the tendon material into or onto a disc to strengthen the annulus fibrosis or to augment or replace the nucleus pulpous.

2. The method of claim 1, further including the steps of:

forming a passageway through the annulus fibrosis of a disc and transplanting the tendon material into the disc through the passageway.

3. The method of claim 1, further including the step of adding one or more therapeutic substances to the tendon material.

4. The method of claim 3, wherein the therapeutic substances include one or more of the following:

culture media, growth factors, differentiation factors, hydrogels, polymers, antibiotics, anti-inflammatory medications, or immunosuppressive medications.

5. The method of claim 1, wherein the tendon material includes palmaris longus tissue.

6. The method of claim 1, further including the steps of treating and/or banking the tendon material to prevent disease transmission and graft rejection.

7. An engineered annulus fibrosis according to the method of claim 1.

8. The engineered annulus fibrosis of claim 7, further including one or more therapeutic substances.

9. The engineered annulus fibrosis of claim 8, wherein the therapeutic substances include one or more of the following:

culture media, growth factors, differentiation factors, hydrogels, polymers, antibiotics, anti-inflammatory medications, or immunosuppressive medications.

10. The method of claim 1, further comprising the steps of:

harvesting fibrocytes, annulus fibrosis cells, cells that differentiate into annulus fibrosis cells, or cells that function like annulus fibrosis cells;

harvesting the extracellular matrix of an annulus fibrosis;

combining the harvested cells with the extracellular matrix; and transplanting the harvested cells and matrix into or onto a disc receiving the tendon material to produce an engineered annulus fibrosis.

11. An engineered annulus fibrosis according to the method of claim 10.

12. The engineered annulus fibrosis of claim 11, further including one or more therapeutic substances.

13. The engineered annulus fibrosis of claim 12, wherein the therapeutic substances include one or more of the following:

culture media, growth factors, differentiation factors, hydrogels, polymers, antibiotics, anti-inflammatory medications, or immunosuppressive medications.

* * * * *